United States Patent [19]

Picone et al.

[11] Patent Number: 5,244,786
[45] Date of Patent: Sep. 14, 1993

[54] METHOD OF MEASURING AVAILABLE FREE THYROXINE BENDING SITES

[75] Inventors: Teresa K. Picone, Vallejo; Stephen B. Friedman, Green Valley Suisun, both of Calif.

[73] Assignee: Microgenics Corporation, Concord, Calif.

[21] Appl. No.: 568,644

[22] Filed: Aug. 13, 1990

Related U.S. Application Data

[63] Continuation of Ser. No. 104,342, Oct. 2, 1987, abandoned.

[51] Int. Cl.$^5$ .............................................. C12Q 1/00
[52] U.S. Cl. .................................... 435/7.9; 435/14; 436/500; 436/501
[58] Field of Search ................. 435/18, 7.9, 7.7, 7.6, 435/975; 436/500, 501, 537, 517, 808

[56] References Cited

U.S. PATENT DOCUMENTS 4,171,244 10/1979 Blakemore et al. ................. 435/188
4,341,865 7/1982 Voss ........................................ 435/7
4,708,929 11/1987 Henderson ............................. 435/7
4,786,591 11/1988 Draeger et al. ..................... 430/548

FOREIGN PATENT DOCUMENTS

0062277A1 3/1982 European Pat. Off. .
WO86/02666 9/1986 PCT Int'l Appl. .

*Primary Examiner*—Sam Rosen
*Attorney, Agent, or Firm*—Cooley Godward Castro Huddleson & Tatum

[57] ABSTRACT

The present invention provides an improved assay for measuring thyroxine uptake by thyroxine binding globulin in which thyroxine binding globulin (TBG) activity is measured directly. The method comprises combining a sample in an aqueous solution with an enzyme donor (ED) conjugated to an analogue of polyiodothyronine that competes with thyroxine for thyroxine binding globulin binding sites. An enzyme acceptor (EA) characterized by providing a modulated enzyme activity in relation to the amount of TBG activity is combined with an enzyme donor and sample in an aqueous solution. The amount of enzyme activity in comparison to a control solution having a known amount of available TBG binding sites is determined.

3 Claims, No Drawings

METHOD OF MEASURING AVAILABLE FREE THYROXINE BENDING SITES

This application is a continuation of U.S. application Ser. No. 07/104,342, filed Oct. 2, 1987, now abandoned.

TECHNICAL FIELD

The present invention relates to diagnostic assays, and in particular to an assay for thyroid uptake.

BACKGROUND

The active thyroid hormones are designated T-4 and T-3. In the blood, T-4 and T-3 are almost entirely bound to plasma proteins. Thyroxine binding globulin (TBG) is normally the major determinant of overall binding intensity of T-4. The interaction between T-4 and its binding proteins is in reversible binding equilibrium. Only a small portion, usually about 0.03 percent of T-4 is free in blood. However, T-3 is not as readily bound, and as a consequence, the normal proportion of free T-3 is eight to ten times greater than that of T-4. Only free (unbound) hormone is available to tissues. Therefore, the metabolic state of the patient correlates more closely with the concentration of free hormone, rather than the total concentration of hormone, in plasma.

There are two general types of disturbances of the thyroid hormone-plasma protein interaction. In the first type of disturbance, an increased amount of TBG or other serum binding proteins or the appearance of abnormal serum binding proteins results in a lowered free hormone level. Total hormone concentration in serum may then increase until the concentration of free hormone is restored to normal. In the second type of disturbance, the concentration of thyroxine-binding globulin (TBG) is normal, but the amount of thyroid hormone is abnormal. In this type of disorder, the proportion of free hormone changes in the same direction as the change in hormone supply.

When the amount of free T-4 is too low, patients can be treated with synthetic T-4 (levothyroxine). In that case it is important to determine how much administered synthetic T-4 will be bound by TBG, rather than the total thyroxine concentration after administration of T-4, since only unbound hormone is effective in treating the patient.

A number of assays related to hormone concentration and binding in blood have been developed. Free T-4 concentration can be measured by equilibrium dialysis of serum enriched with a small amount of labeled T-4. The percent of T-4 that is dialyzable, and therefore free, is determined. From that number, the percentage that is bound can be calculated. However, the dialysis technique is cumbersome and has not generally been useful for clinical purposes. An in vitro uptake test in which serum is incubated with labeled T-4 or T-3 and then with an insoluble particulate matter such as resin or charcoal that non-specifically binds free hormone has also been developed. The percentage of labeled hormone associated with the particulate matter varies inversely with the concentration of unoccupied sites among serum proteins and their affinity for the labeled hormone.

Methods which would more accurately determine uptake values of TBG would assist the clinician in differentiating low T-4 state of a non-thyroidal illness from overt thyroxine deficiency of hypothyroidism. Such methods would also allow the clinician to more accurately determine the amount of synthetic T-4 to administer to alleviate symptoms produced by hypothyroid disease.

DESCRIPTION OF THE RELEVANT LITERATURE

Kaptein et al., J. of Clin. Endrocrinol. and Metab. (1981) 52:1073 provides a comparison of eight methods of making free thyroxine estimates. The article describes the ability of the assays to distinguish low T-4 levels caused by hypothyroid and hypothalamic-pituitary diseases from those caused by non-thyroidal illnesses. The evaluated assay methods were equilibrium dialysis, enzyme immunoassay (Abbott), antibody-coated tube (Clinical Assays), antibody-coated microfine silica (Corning Immunophase), microencapsulated antibody (Damon) and free T-4 uptake using the T-3 uptake ratio or the thyroxine binding globulin method.

SUMMARY OF THE INVENTION

The present invention provides an improved method of measuring thyroxine uptake in which thyroxine binding globulin (TBG) activity is measured directly. A method of measuring thyroxine uptake by TBG in a sample comprises combining the sample in an aqueous solution with an enzyme donor (ED) conjugated to an analogue of polyiodothyronine that binds with available thyroxine binding globulin sites. Attachment of T-4 to ED is controlled so that the affinity of TBG for T-4 is not altered significantly. The sample is combined with an enzyme donor (ED) and an enzyme acceptor (EA) characterized by providing a modulated enzyme activity in relation to the amount of TBG activity. The amount of enzyme activity in comparison to a control solution having a known amount of available TBG binding sites is determined.

The instant method is faster, more precise, and simpler to perform in addition to being more accurate and economical than indirect measurement methods in which binding is measured using antibodies.

DESCRIPTION OF SPECIFIC EMBODIMENTS

An improved method is provided of measuring thyroxine uptake in which thyroxine binding globulin (TBG) activity is measured directly. The present method provides reliable information as to whether low levels of free T-3 and/or T-4 in the serum are due to hypothyroidism or to non-thyroidal illness.

The method comprises combining a sample in an aqueous solution with an enzyme donor conjugated to an analogue of polyiodothyronine that binds with available thyroxine binding globulin sites. The enzyme acceptor, the enzyme donor and enzyme substrate are combined with the sample to form an assay medium. The sample may be pre-incubated with either the enzyme donor conjugate or the enzyme acceptor. Alternatively, all components of the assay medium may be combined so long as the enzyme donor and the enzyme acceptor are not mixed in the absence of sample. The enzyme acceptor is characterized, in part, by providing a modulated enzyme activity in relation to the amount of TBG activity when bound to the conjugate. That is, the amount of enzyme activity decreases as the TBG activity of the sample increases. The amount of enzyme activity is compared to a control solution having a known amount of thyroxine uptake by TBG.

The assay method can be used with any sample containing thyroxine binding globulin. Usually the sample will be patient serum or plasma. Other than removal of particulates, no other pretreatment of the sample will usually be performed for purposes of the instant assay method.

The enzyme donor and enzyme acceptor are partial sequences of β-galactosidase, the enzyme donor being smaller. The enzyme donor and the enzyme acceptor can be mutated. The β-galactosidase enzyme donor fragment has substantially the same amino acid sequence as the N-terminal portion of the β-galactosidase monomer, the enzyme acceptor has substantially the same or the same sequence as the C-terminus, being more than 50% of the β-galactosidase monomer molecule. β-Galactosidase activity results upon complementation of the enzyme donor conjugate with the β-galactosidase enzyme acceptor monomer fragment.

The enzyme acceptor is characterized by providing in conjunction with the enzyme donor conjugate a complex whose enzyme activity varies in relation to the amount of thyroxine binding globulin activity under the conditions of the assay. That is, when the enzyme donor conjugate is bound to TBG, the enzyme activity during the time of measurement is substantially reduced in comparison to the enzyme activity when the enzyme donor conjugate is unbound.

The enzyme donor fragment is conjugated to an analogue of polyiodothyronine that binds to thyroxine binding globulin binding sites (sometimes referred to as a moiety that binds to such sites). The analogue is usually T-4 or related to T-4. T-3 may also be used; however, TBG has a much lower affinity for T-3, depending on the ED used, leading to less accurate measurements. For the most part, the analogue will have a 4-(3',5'-diiodo-4'-hydroxyphen-1'-oxy)-3,5-diiodophenyl group.

β-galactosidase enzyme donors and acceptors are described in U.S. Pat. No. 4,708,929 (application Ser. No. 721,267 filed Apr. 8, 1985), which disclosure is incorporated herein by reference. The conditions of the assay described in that application are applicable to the subject invention.

The aqueous solution and assay conditions provide for complementation between enzyme donor and enzyme acceptor. In general, physiological buffers such as sodium phosphate buffer are useful. A preferred buffer comprises 10 to 30 mM $NaPO_4$, 5 to 10 mM EGTA, and 10 to 20 mM $NaN_3$ having a pH of between 6 and 8. The temperature will usually be at least at 25° C., preferably elevated, but below 60°, usually below 70° C. Enzyme assays are generally conducted at room temperature (25° C.) to less than 40° C., usually about 37° C. The assays are performed at atmospheric pressure.

The concentration of enzyme donor conjugates in the assay medium will usually be in the range of about 1 to 60 nM, more usually 5 to 25 nM, while the enzyme acceptor concentration will be 40 to 200 units/ml, usually 80 to 120 units/ml. The molar ratios of enzyme donor conjugate to enzyme acceptor will usually be 1:30 to 1:80 usually 1:50 to 1:60. The usual range of interest for quantitation of TBG binding sites will be 20 to 50% uptake.

The amount of enzyme activity in the assay medium will be determined in accordance with standard techniques for measuring β-galactosidase activity. An enzyme substrate is employed that when cleaved by the enzyme results in a change in the amount of light absorbance or emission of the assay medium. That is, cleavage of the substrate results in the appearance or disappearance of a colored or a fluorescent product. A preferred enzyme substrate is ortho-nitrophenyl-β-galactoside (ONPG) which is enzymatically cleaved to form ortho-nitrophenol (ONP). ONP absorbance values are measured at 420 nm. Other comparable enzyme substrates are also commercially available.

Determining the amount of TBG activity in comparison to a sample having a known amount of TBG activity can be performed in a number of ways. Conveniently the rate of change of absorbance in a known sample can be compared to the rate of change in the unknown. One or more unknown samples and a control sample (standard), usually two or three standards, are assayed. The sample(s) and the controls are processed in parallel in the following way. An initial reading at about 3 to about 4 minutes after mixing the sample is performed. The samples are incubated for an additional 1 to 2 minutes. The second absorbance values are read. The change in absorbance or emission values of the standards can be used to prepare a standard curve. The unknown TBG binding site value is determined in relation to the standard curve. In this way, the percentage of T-4 uptake in a sample can be determined from the curve.

A kit containing reagents facilitating the present invention is also contemplated. The kit comprises in at least one container, usually separate containers, a β-galactosidase enzyme donor conjugate as described above, and an enzyme acceptor. When packaged in separate containers, the enzyme donor or enzyme acceptor may additionally contain enzyme substrate. The enzyme donor conjugate and enzyme acceptor and substrate may be present in lyophilized form. The kit will usually contain a buffer suitable for reconstituting the reagents, which may be packaged with the enzyme components or separately. The kit may also contain one or more control samples comprising serum having a known amount of thyroxine uptake by thyroxine binding globulin. The kit can be particularly designed for use with autoanalyzers.

The following examples are offered by way of illustration for purposes of clarity and not by way of limitation.

EXPERIMENTAL

Buffered solutions were prepared of 11 nM enzyme donor conjugate (ED4-T4, see application Ser. No. 721,267, supra) in ED buffer (20 mM $NaPO_4$; 10 mM EGTA (ethylene-bis-oxyethylenenitrilo tetraacetic acid); 20 mM $NaN_3$; 0.05% Tween 20; 6.25 mg/ml ONPG; 0.9% N-lauroylsarcosine, Na salt pH 7.0) and 22 units of enzyme acceptor (EA-22) in EA buffer (20 mM $NaPO_4$; 10 mM EGTA; 20 mM $NaN_3$; 5 mM Sucrose; 2 mM $Mg(OAC)_2$ 4 $H_2O$; 0.2% β-cyclodextrin 3.6% Glycerol; pH 7.0). Both solutions were stored on ice until used. Additionally, control serum samples were used as calibrators. The value of the calibrators was 20, 35 and 50 percent T-uptake. Two patient samples having an unknown TBG activity were also assayed.

14 μl of each known serum standard was pipetted into a labeled well of a 96 well microtiter plate. 14 μl of each unknown serum was also added to a well of a 96 well microtiter plate. 14 μl of distilled water was added to one well to serve as a blank. 36 μl of distilled water was added to each microtiter well. 160 μl of enzyme acceptor solution was added to each well except the blank which received 160 μl of distilled water. The solutions were mixed by either tapping the plate or rotating the plate. Thereafter, 40 μl of enzyme donor solution was placed in each well. The solutions were mixed by tapping or rotating the plate. The plate was placed in a 37° C. incubator for four minutes. The microtiter plate was removed from the incubator and absorbance values at 420 nm were read for each sample using a microtiter plate reader with the appropriate filter. Immediately after reading the plate, it was returned to the incubator. A second absorbance reading for each well was taken one minute after the first reading, five minutes total time and the difference between the values determined. A standard curve for the known standards using known uptake values as the X-axis and the one-minute rate as the Y-axis was constructed. The rate of the unknown sample was read off of the curve to determine the percentage of T-uptake.

The above results demonstrate a facile, accurate and rapid direct determination of available binding sites of TBG. The method does not require indirect determinations involving excess thyroxine to equilibriate the specimen and determine total binding site in addition to determining total thyroxine nor the use of radioisotopes. The TBG is able to bind to the enzyme donor conjugate so as to permit a direct measurement of available TBG sites.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for directly measuring available thyroxin binding sites in a sample, comprising:

(a) combining in an assay medium (1) a β-galactosidase substrate, (2) said sample, (3) a β-galactosidase acceptor fragment having substantially the same amino acid sequence as a C-terminus region of β-galactosidase, and (4) a β-galactosidase enzyme donor conjugate comprising a β-galactosidase enzyme donor fragment, wherein said donor fragment has substantially the same amino acid sequence as an N-terminus region of β-galactosidase complementary to said C-terminus region, linked to a moiety that competes with thyroxin for free thyroxin binding sites, with the proviso that said β-galactosidase donor conjugate and said β-galactosidase acceptor fragment are not combined in the absence of said sample, and wherein said donor and acceptor fragments form an active β-galactosidase enzyme upon complexation, said complexation being modulated if said enzyme donor conjugate binds to a protein having a thyroxin binding site; and (b) determining the amount of β-galactosidase activity in said assay medium as compared to an assay medium containing a known amount of available thyroxin binding sites.

2. A method according to claim 1, wherein said moiety is a polyiodothyronine.

3. A method according to claim 1, wherein said sample is serum or plasma.

* * * * *